(12) United States Patent
Zhu et al.

(10) Patent No.: US 11,602,594 B2
(45) Date of Patent: Mar. 14, 2023

(54) DEVICE, APPARATUS AND METHOD FOR CONTROLLING INFUSION (71) Applicants: HEFEI BOE OPTOELECTRONICS TECHNOLOGY CO., LTD., Hefei (CN); BOE TECHNOLOGY GROUP CO., LTD., Beijing (CN)

(72) Inventors: Zhengwei Zhu, Beijing (CN); Yanfei Guo, Beijing (CN); Jiong Huang, Beijing (CN)

(73) Assignees: HEFEI BOE OPTOELECTRONICS TECHNOLOGY CO., LTD., Hefei (CN); BOE TECHNOLOGY GROUP CO., LTD., Beijing (CN)

( * ) Notice: Subject to any disclaimer, the term of this patent is extended or adjusted under 35 U.S.C. 154(b) by 805 days.

(21) Appl. No.: 16/470,355

(22) PCT Filed: Dec. 14, 2018

(86) PCT No.: PCT/CN2018/121176
§ 371 (c)(1),
(2) Date: Jun. 17, 2019

(87) PCT Pub. No.: WO2019/174340
PCT Pub. Date: Sep. 19, 2019

(65) Prior Publication Data
US 2021/0353856 A1 Nov. 18, 2021
US 2022/0313906 A9 Oct. 6, 2022

(30) Foreign Application Priority Data

Mar. 16, 2018 (CN) .......................... 201810216741.1

(51) Int. Cl.
*A61M 5/168* (2006.01)
*A61M 5/14* (2006.01)
*A61M 5/44* (2006.01)

(52) U.S. Cl.
CPC ...... *A61M 5/16877* (2013.01); *A61M 5/1408* (2013.01); *A61M 5/1684* (2013.01);
(Continued)

(58) Field of Classification Search
CPC ............ A61M 5/16877; A61M 5/1408; A61M 5/16813
See application file for complete search history.

(56) References Cited

U.S. PATENT DOCUMENTS 4,010,749 A * 3/1977 Shaw ................ A61M 5/16836
222/54
4,616,801 A * 10/1986 Cewers ............. A61M 5/16813
251/9

(Continued)

FOREIGN PATENT DOCUMENTS

CN 2577853 Y 10/2003
CN 101961515 A 2/2011
(Continued)

OTHER PUBLICATIONS

China First Office Action, Application No. 201810216741.1, dated Apr. 20, 2020, 31 pps.: with English translation.
(Continued)

*Primary Examiner* — Jenna Zhang
(74) *Attorney, Agent, or Firm* — Armstrong Teasdale LLP (57) ABSTRACT Embodiments of the present disclosure provide a device, an apparatus, and a method for controlling infusion. The device may include a multi-port container assembly and a liquid flow controller. The multi-port container assembly includes a multi-port container having a plurality of inlets and an outlet, a detector configured to detect amount of liquid in the multi-port container, a first communication subassembly, and a first controller. The first controller may send a first signal to the liquid flow controller via the first communica-
(Continued)

tion subassembly in response to the detector detecting that the amount of liquid is lower than a first predetermined threshold. The liquid flow controller may turn off a first infusion tube currently used and turn on a next first infusion tube in response to receiving the first signal.

16 Claims, 7 Drawing Sheets

(52) U.S. Cl.
CPC .......... *A61M 5/16813* (2013.01); *A61M 5/44* (2013.01); *A61M 2205/3368* (2013.01); *A61M 2205/3386* (2013.01); *A61M 2230/06* (2013.01)

(56) References Cited

U.S. PATENT DOCUMENTS

| | | | | |
|---|---|---|---|---|
| 2004/0254527 | A1* | 12/2004 | Vitello | B41J 2/17513 604/82 |
| 2007/0060874 | A1* | 3/2007 | Nesbitt | A61M 5/1408 604/80 |
| 2011/0319813 | A1* | 12/2011 | Kamen | A61M 5/14244 604/151 |
| 2014/0309617 | A1 | 10/2014 | Ambrosina et al. | |

FOREIGN PATENT DOCUMENTS

| | | |
|---|---|---|
| CN | 202223641 U | 5/2012 |
| CN | 102743809 A | 10/2012 |
| CN | 203060439 U | 7/2013 |
| CN | 203196059 U | 9/2013 |
| CN | 103845778 A | 6/2014 |
| CN | 104014031 A | 9/2014 |
| CN | 204158813 U | 2/2015 |
| CN | 204293623 U | 4/2015 |
| CN | 204337400 U | 5/2015 |
| CN | 104784776 A | 7/2015 |
| CN | 204484916 U | 7/2015 |
| CN | 204709522 U | 10/2015 |
| CN | 204910329 U | 12/2015 |
| CN | 205055061 U | 3/2016 |
| CN | 105457130 A | 4/2016 |
| CN | 105498021 A | 4/2016 |
| CN | 205215859 U | 5/2016 |
| CN | 205569439 U | 9/2016 |
| CN | 205796135 U | 12/2016 |
| CN | 106421984 A | 2/2017 |
| CN | 106563187 A | 4/2017 |
| CN | 206081223 U | 4/2017 |
| CN | 106924840 A | 7/2017 |
| CN | 106964022 A | 7/2017 |
| CN | 107261252 A | 10/2017 |
| CN | 206548946 U | 10/2017 |
| CN | 206714994 U | 12/2017 |
| CN | 107583138 A | 1/2018 |
| CN | 107596495 A | 1/2018 |
| CN | 107596502 A | 1/2018 |
| WO | 9207595 A1 | 5/1992 |
| WO | 2017012781 A1 | 1/2017 |
| WO | 2017089615 A1 | 6/2017 |

OTHER PUBLICATIONS

China Second Office Action, Application No. 201810216741.1, dated Sep. 9, 2020, 31 pps.: with English translation.
China Third Office Action, Application No. 201810216741.1, dated Feb. 19, 2021, 32 pps.: with English translation.
PCT International Search Report, Application No. PCT/CN2018/121176, dated Mar. 13, 2019, 8 pages: with English translation.
PCT Written Opinion, Application No. PCT/CN2018/121176, dated Mar. 13, 2019, 6 pages.: with English translation of relevant part.

* cited by examiner

DEVICE, APPARATUS AND METHOD FOR CONTROLLING INFUSION

CROSS REFERENCE TO RELATED APPLICATIONS

This patent application is a National Stage Entry of PCT/CN2018/121176 filed on Dec. 14, 2018, which claims the benefit and priority of Chinese Patent Application No. 201810216741.1 filed on Mar. 16, 2018, the disclosures of which are incorporated by reference herein in their entirety as part of the present application.

BACKGROUND

The present disclosure relates to a field of infusion control, and more particularly, to a device for controlling infusion, an apparatus for controlling infusion, and a method for controlling infusion.

As a conventional medical health treatment method and means, infusion is widely used in modern medical treatment. Currently, a plurality of vials of medicament are typically required for infusion, and generally different medicament cannot be mixed. According to a traditional infusion method, at the end of a vial of medicament, patient or their carer may remind medical personnel to switch to a next vial, otherwise, the medical personnel may wait around the patient for some more time and switch the vials until the current medicament are completely infused into the patient, thereby invisibly increasing work intensities and energies of the medical personnel, the patient, and the carer. In a crowded care unit, patients' health conditions are different, thus it is difficult for the medical personnel to look after every patient receiving infusion. Therefore, medical risks and disputes may be caused by failure of timely adjustment of infusion speed or failure of timely switching at the end of infusion.

BRIEF DESCRIPTION

Embodiments of the present disclosure provide a device for controlling infusion (hereinafter referred to as an infusion control device), an apparatus for controlling infusion (hereinafter referred to as an infusion control apparatus), and a method for controlling infusion (hereinafter referred to as an infusion control method).

A first aspect of the present disclosure provides a device for controlling infusion, which includes a multi-port container assembly and a liquid flow controller. The multi-port container assembly may include a multi-port container, a detector, a first communication subassembly, and a first controller. The multi-port container has a plurality of inlets and an outlet, wherein each of the inlets is connected with an infusion container via a first infusion tube, and the outlet is connected with an infusion needle via a second infusion tube. The detector is configured to detect amount of liquid in the multi-port container. The first communication subassembly is communicatively coupled to a liquid flow controller. The first controller is coupled to the detector and the first communication subassembly, and is configured to send a first signal to the liquid flow controller via the first communication subassembly in response to the detector detecting that the amount of liquid is lower than a first predetermined threshold. The liquid flow controller is configured to turn on or off the first infusion tube in response to receiving the first signal from the first communication subassembly.

In some exemplary embodiments, the liquid flow controller may be further configured to turn off the first infusion tube currently used and turn on a next first infusion tube in response to receiving the first signal from the first communication subassembly.

In some exemplary embodiments, the liquid flow controller includes a plurality of the liquid flow controllers, and each of the liquid flow controllers may control to turn on or off the first infusion tube.

In some exemplary embodiments, the device may further include a wearable component. The wearable component is configured to detect a pulse of a person receiving infusion, and send a second signal to the liquid flow controller in response to detecting an abnormal pulse of the person receiving infusion. The liquid flow controller may be further configured to reduce an infusion speed in the first infusion tube currently used in response to receiving the second signal from the wearable component.

In some exemplary embodiments, the multi-port container assembly may further include a first temperature sensor and a first heating and thermal insulation layer. The first temperature sensor is coupled to the first controller and is configured to detect temperature of liquid in the multi-port container and transmit the detected temperature to the first controller. The first heating and thermal insulation layer is coupled to the first controller and is configured to heat the liquid in the multi-port container under control of the first controller. The first controller is further configured to control the first heating and thermal insulation layer to heat the liquid in the multi-port container in response to the temperature of the liquid in the multi-port container detected by the first temperature sensor being lower than a second predetermined threshold.

In some exemplary embodiments, each of the liquid flow controllers may include a holder having an open slot, an eccentric wheel, a micromotor, a second communication subassembly, and the second controller. For the holder having the open slot, the first infusion tube is placed in the open slot. The eccentric wheel is configured to turn on or off the first infusion tube, or regulate an infusion speed in the first infusion tube by compressing or releasing the first infusion tube by way of rotatably going into/out of the open slot. The micromotor is configured to drive the eccentric wheel to rotate under control of the second controller. The second communication subassembly is communicatively coupled to the first communication subassembly. The second controller is coupled to the micromotor and the second communication subassembly, and is configured to control the micromotor to drive the eccentric wheel to rotate to turn on or off the first infusion tube in response to receiving the first signal from the first communication subassembly via the second communication subassembly.

In some exemplary embodiments, each of the liquid flow controllers may further include a timing component. The timing component is configured to start timing under the control of the second controller and notify the second controller when a preset time value is reached. The second controller may be further configured to control the timing component to start timing in response to receiving the first signal from the first communication subassembly, and control to turn on the corresponding first infusion tube in response to receiving a notification from the timing component indicating that the timing reaches the preset time value.

In some exemplary embodiments, the wearable component may include a pulse sensor, a third communication subassembly, and a third controller. The pulse sensor is configured to detect a pulse of a person receiving infusion. The third communication subassembly is communicatively coupled to the liquid flow controller. The third controller is coupled to the pulse sensor and the third communication subassembly, and is configured to send the second signal to the liquid flow controller via the third communication subassembly in response to detecting the abnormal pulse of the person receiving infusion by the pulse sensor.

In some exemplary embodiments, the wearable component may further include a second temperature sensor and a second heating and thermal insulation layer. The second temperature sensor is configured to detect temperature of the infusion liquid near the infusion needle and transmit the detected temperature to the third controller. The second heating and thermal insulation layer is configured to heat the infusion liquid near the infusion needle under control of the third controller. The third controller is further coupled to the second temperature sensor and the second heating and thermal insulation layer, and is further configured to control the second heating and thermal insulation layer to heat the infusion liquid near the infusion needle in response to the temperature detected by the second temperature sensor being lower than a third predetermined threshold.

In some exemplary embodiments, the detector includes a pressure sensor. The amount of liquid is represented by a liquid pressure of the multi-port container detected by the pressure sensor.

Another aspect of the present disclosure further provides an apparatus for controlling infusion, which includes a device for controlling infusion according to any one embodiment of the present disclosure and a monitoring device. The monitoring device is configured to receive and present at least one of amount of liquid in the multi-port container detected by the detector from the multi-port container assembly and temperature of the liquid in the multi-port container detected by the first temperature sensor of the multi-port container assembly, and/or receive and present at least one of a pulse of a person receiving infusion detected by the pulse sensor of the wearable component and temperature of the liquid for infusion near the infusion needle detected by the second temperature sensor of the wearable component.

In some exemplary embodiments, the monitoring device is further configured to receive a first predetermined threshold preset by a user, and send the first predetermined threshold to the multi-port container assembly, receive an infusion sequence of a first infusion tube preset by the user, and send the infusion sequence to a liquid flow controller, receive a second predetermined threshold preset by the user, and send the second predetermined threshold to the multi-port container assembly, receive a third predetermined threshold preset by the user, and send the third predetermined threshold to the wearable component, and receive a preset time value preset by the user and send the preset time value to the liquid flow controller.

Still another aspect of the present disclosure also provides a method for controlling infusion. In this method, a detector detects amount of liquid in a multi-port container, wherein the multi-port container has a plurality of inlets and an outlet, each of the inlets is connected with an infusion container via a first infusion tube, and the outlet is connected with an infusion needle via a second infusion tube. A first signal is sent to a liquid flow controller in response to the detector detecting that the amount of liquid is lower than a first predetermined threshold, and the liquid flow controller turns on or off the first infusion tube in response to receiving the first signal.

In some exemplary embodiments, the turning on or off the first infusion tube by the liquid flow controller in response to receiving the first signal includes turning off the first infusion tube currently used and turning on a next first infusion tube by the liquid flow controller in response to receiving the first signal.

In some exemplary embodiments, the liquid flow controller includes a plurality of the liquid flow controllers, and each of the liquid flow controllers is configured to control to turn on or off the first infusion tube. The turning off or on the first infusion tube by the liquid flow controller in response to receiving the first signal includes starting timing by a timing component in response to receiving the first signal, and turning on the corresponding first infusion tube in response to the timing component indicating that the timing reaches a preset time value.

In some exemplary embodiments, the method further includes detecting, by a wearable component, a pulse of a person receiving infusion, and sending, by the wearable component, a second signal to the liquid flow controller in response to detecting an abnormal pulse of the person receiving infusion, and reducing, by the liquid flow controller, an infusion speed in the first infusion tube currently used in response to receiving the second signal from the wearable component.

In some exemplary embodiments, the method further includes detecting, by a first temperature sensor, temperature of liquid in the multi-port container, and heating, by a first heating and thermal insulation layer, the liquid in the multi-port container in response to the temperature of the liquid in the multi-port container detected by the first temperature sensor being lower than a second predetermined threshold.

In some exemplary embodiments, the method further includes detecting, by a second temperature sensor, temperature of the liquid for infusion near the infusion needle, and heating, by a second heating and thermal insulation layer, the infusion liquid near the infusion needle in response to the temperature detected by the second temperature sensor being lower than a third predetermined threshold.

In some exemplary embodiments, the method further includes at least one of presenting amount of liquid in a multi-port container detected by the detector, presenting temperature of the liquid in the multi-port container detected by the first temperature sensor, presenting a pulse of a person receiving infusion detected by the pulse sensor, and presenting temperature of the infusion liquid near the infusion needle detected by the second temperature sensor.

DETAILED DESCRIPTION

In order that those skilled in the art better understand the technical solution of the present disclosure, the technical solution for controlling infusion provided by specific embodiments of the present disclosure are further described in detail below with reference to the accompanying drawings. Apparently, the described and illustrated embodiments and various specific features thereof merely serve as exemplary description of the present disclosure instead of limitations on the present disclosure. All other embodiments and specific features thereof obtained by those of ordinary skill in the art based on the exemplary description without creative efforts shall fall within the protection scope of the present disclosure.

Figure 1:
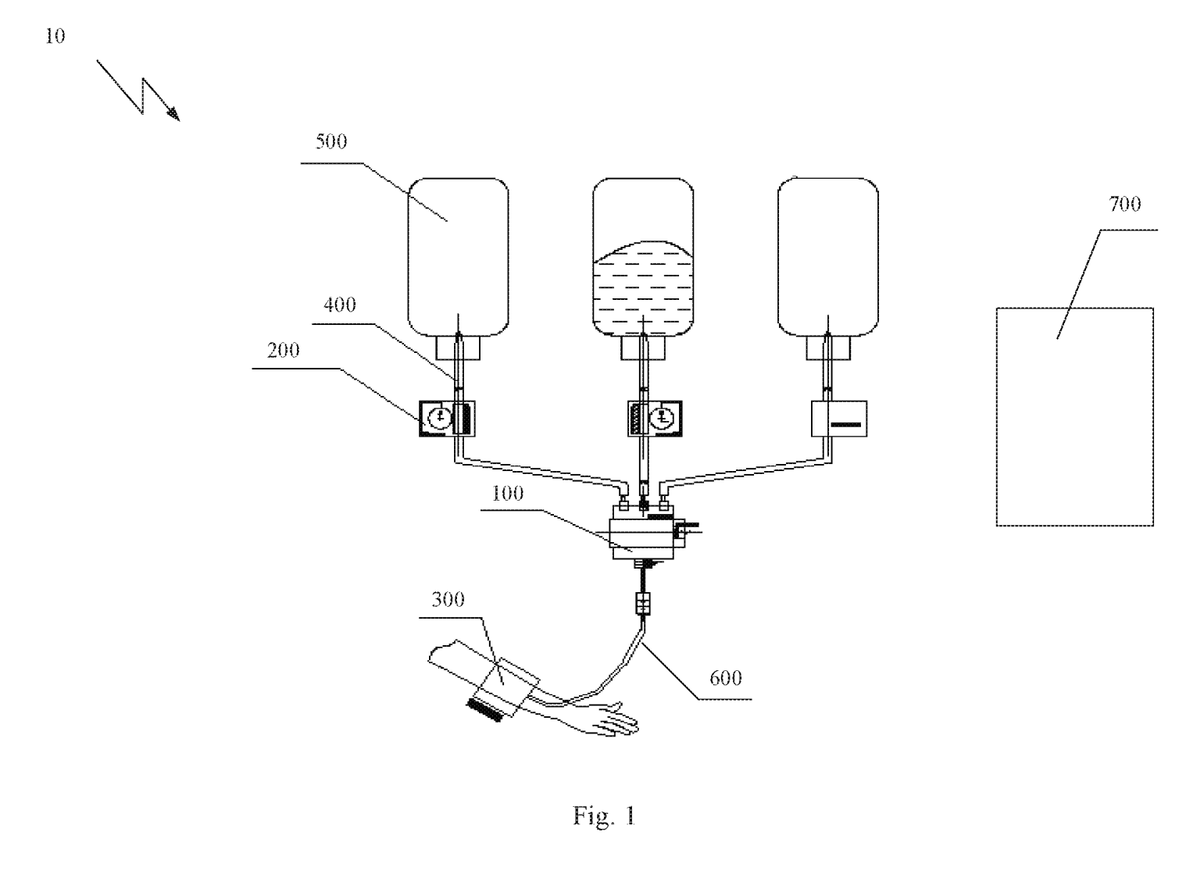
FIG. 1 illustrates a schematic structural diagram of an infusion control device according to an embodiment of the present disclosure.

Now referring to FIG. 1, a schematic structural diagram of an infusion control device 10 according to an embodiment of the present disclosure is provided. As shown in FIG. 1, in some embodiments, the infusion control device 10 may include a multi-port container assembly 100 and a liquid flow controller 200.

The multi-port container assembly 100 is configured to respectively connect with a plurality of infusion containers (e.g., infusion bottles, infusion bags, or the like) 500 through a plurality of first infusion tubes 400, and connect with an infusion needle through a second infusion tube 600. Therefore, the multi-port container assembly 100 can cooperate with the liquid flow controller 200 to implement switching between the plurality of infusion containers 500.

The liquid flow controller 200 may be located on the first infusion tube 400 and may be configured to sequentially turn off or on the first infusion tubes 400, such that switching between the plurality of infusion containers can be realized.

In some embodiments, the liquid flow controller 200 may include a plurality of the liquid flow controllers 200. Each of the liquid flow controllers 200 may be positioned on a first infusion tube 400 and may be configured to turn on or off the first infusion tube 400.

In some further embodiments, the liquid flow controller 200 may be configured to not only turn on or off the first infusion tube 400, but also regulate infusion flow rate in the first infusion tube 400. For example, the liquid flow controller 200 may reduce the infusion flow rate in the first infusion tube 400 in response to an abnormal pulse of the person receiving infusion, as described below.

Figure 2:
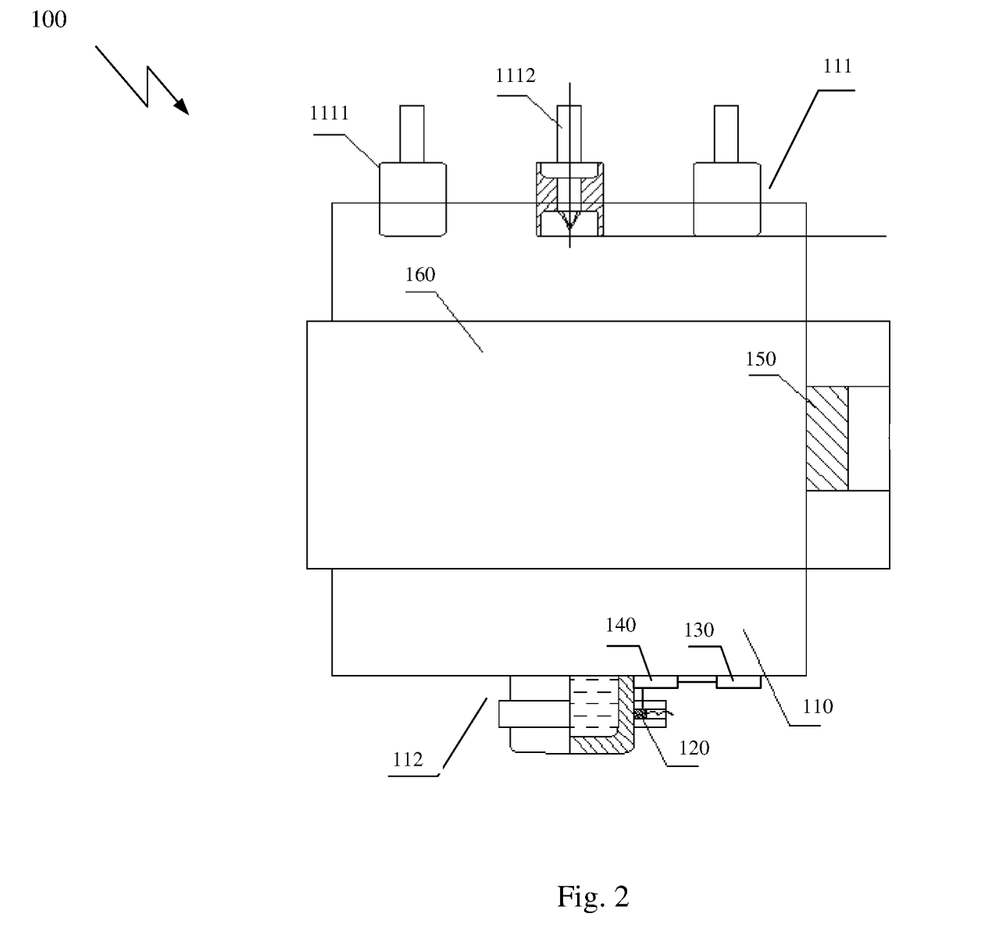
FIG. 2 illustrates a schematic structural diagram of a multi-port container assembly according to an embodiment of the present disclosure.

Now referring to FIG. 2, a schematic structural diagram of a multi-port container assembly 100 according to an embodiment of the present disclosure is illustrated. As shown in FIG. 2, the multi-port container assembly 100 may include a multi-port container 110, a detector 120, a first communication subassembly 130, and a first controller 140.

The multi-port container 110 may have a plurality of inlets 111 and an outlet 112. The respective inlets 111 are connected with an infusion container 500 via a first infusion tube 400. The outlet 112 is connected with an infusion needle via a second infusion tube 600. A rubber stopper 1111 may be arranged at each of the inlets 111 to facilitate insertion of the infusion needle 1112 at the end of the first infusion tube 400. Then connection between the inlet 111 and the infusion container 500 can be implemented via the infusion tube 400. The multi-port container 110 may be made of any material known to those skilled in the art, such as glass, plastic, or the like. The multi-port container 110 may be arranged as a hermetic container with any shape, such as, square, cylinder, or the like, as well as of any suitable size, thickness, and any structure.

The detector 120 may detect amount of liquid in the multi-port container 110. For example, the detector 120 may include a pressure sensor. The pressure sensor may detect a liquid pressure of the multi-port container 110. The amount of liquid in the multi-port container 110 may be represented by the liquid pressure detected by the pressure sensor. The pressure sensor may be any pressure sensor for detecting the liquid pressure known to those skilled in the art. The pressure sensor may be positioned at any location contacting with the liquid in the multi-port container 110, for example, at the outlet 112. In addition, the detector 120 may also include a liquid level meter, such as, a radar liquid level meter, an ultrasonic liquid level meter, and the like. In some embodiments, the amount of liquid in the multi-port container 110 may be represented by the liquid level detected by the liquid level meter.

The first communication subassembly 130 may be communicatively coupled to the liquid flow controller 200. The first communication subassembly 130 may be any wireless communication assembly known to those skilled in the art, such as, a Bluetooth communication assembly, a WLAN communication assembly, etc. The first communication subassembly 130 may establish a wireless connection between the respective communication subassemblies in the liquid flow controller 200, such that they can communicate to each other. In some embodiments, the first communication subassembly 130 may also be a wired communication subassembly, which establishes a wired connection between the respective wired communication subassemblies in the liquid flow controller 200 via a wired line, such that they can communicate to each other. The first communication subassembly 130 may be positioned at any location on the multi-port container 110, for example, on an outer wall at the outlet 112 of the multi-port container 110.

The first controller 140 may be coupled to the detector 120 and the first communication subassembly 130. The first controller 140 may be configured to send a first signal to the liquid flow controller 200 via the first communication subassembly 130 in response to the detector 120 detecting that the amount of liquid is lower than a first predetermined threshold. Correspondingly, the liquid flow controller 200 may be configured to turn off a current first infusion tube 400 and turn on a next first infusion tube 400 in response to receiving the first signal from the first communication subassembly 130. That is, when the amount of liquid in the multi-port container 110 detected by the detector 120 is lower than the first predetermined threshold, the first controller 140 may determine that the liquid in the infusion container 500 currently connected with the multi-port container 110 is exhausted. Thus, the first signal may be sent to the liquid flow controller 200 to turn off the current infusion tube 400 and turn on the next infusion tube 400, to continue the infusion for the infusion container 500 connected with the next infusion tube 400. In this way, automatic and timely switching between the infusion containers can be implemented. The continuity and correct sequence of the infusion can be ensured. The medical risks caused by failure of timely switching the infusion containers can be reduced, and the burden on the medical personnel can also be reduced.

The first signal can be any electrical signal that has unique electrical characteristics and thus can be recognized. The first predetermined threshold can be set by a user in advance and stored in the first controller 140, or can be set by a manufacturer and stored in the first controller 140. Specific value of the first predetermined threshold may be determined according to actual infusion experience, or may be calculated according to variation of amount of liquid during infusion. For example, the first predetermined threshold may be determined to be the amount of liquid when height of liquid level is approximately equal to 10 mm. In some embodiments, the first predetermined threshold may be changed by the user according to actual needs during actual use of the device.

The first controller 140 may be implemented by any processing unit having logic operation and processing functions. The processing unit typically has hardware processing circuits or chips, and software for programming the hardware circuits or chips to perform the respective functions. The software may be stored in a memory unit associated with the hardware processing circuits and loaded and executed by the hardware processing circuits, or may be solidified in the hardware processing circuits or chips. For example, the first controller 140 may be implemented by a microcontroller unit (MCU).

The first controller 140 may be coupled to the detector 120 and the first communication subassembly 130 in a hardwired manner. For example, the first controller 140 may be positioned on a same printed circuit board PCB as the detector 120 and the first communication subassembly 130, and may be mounted on an outer wall of the outlet 112 of the multi-port container 110.

In some embodiments, the multi-port container assembly 100 may further include a first temperature sensor 150 and a first heating and thermal insulation layer 160.

The first temperature sensor 150 may be coupled to the first controller 140 (not shown), and may be configured to detect temperature of liquid in the multi-port container 110 and transmit the detected temperature to the first controller 140.

The first heating and thermal insulation layer 160 may be coupled to the first controller 140 (not shown), and may be configured to heat the liquid in the multi-port container 110 under control of the first controller 140.

The first controller 140 may be further configured to control the first heating and thermal insulation layer 160 to heat the liquid in the multi-port container 110 in response to the temperature of the liquid in the multi-port container 110 detected by the first temperature sensor 150 being lower than a second predetermined threshold.

The first temperature sensor 150 may be any temperature sensor known to those skilled in the art. The first temperature sensor 150 may be arranged, for example, on the side wall of the multi-port container 110, and may be in contact with the liquid in the multi-port container 110 through an opening on the side wall of the multi-port container 110, such that the temperature of the liquid in the multi-port container 110 may be measured. As a result, the first temperature sensor may also be arranged at the inlet 111 or the outlet 112 of the multi-port container 110.

For example, the first heating and thermal insulation layer 160 may be arranged to cover the periphery of the multi-port container 110, and may be composed of a layer of thermal insulation material and a heating device embedded into the thermal insulation material. The thermal insulation material may be any material having a thermal insulation function known to those skilled in the art, such as polyurethane, etc. The heating device may be any device having a heating function known to those skilled in the art, such as a resistive heater or a heating controller, and the like.

The first temperature sensor 150 and the first heating and thermal insulation layer 160 may be in wired connection (or wireless connection) to the first controller 140. Therefore, the data for the detected temperature may be transmitted to the first controller 140 and then control instructions from the first controller 140 may be received.

The second predetermined threshold may be set by a user in advance and stored in the first controller 140, or may be set by a manufacturer in advance and stored in the first controller 140. Specific value of the second predetermined threshold may be determined according to the temperature of the liquid as required during infusion. For example, the second predetermined threshold may be determined to be slightly higher than the normal temperature of a human body or other temperatures which is most beneficial to human health. In some embodiments, the second predetermined threshold may be changed by the user according to actual needs during actual use of the device.

Figure 3:
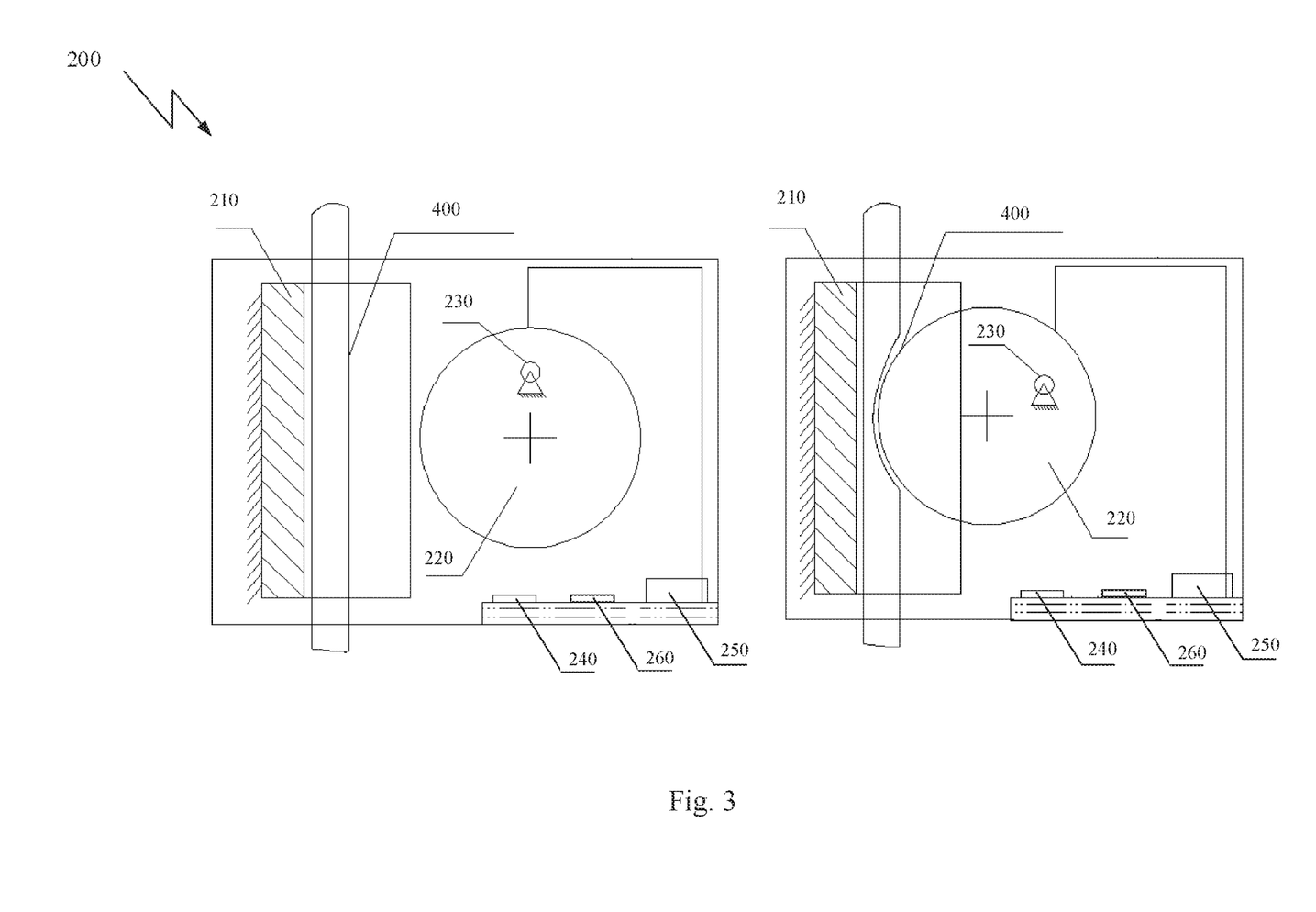
FIG. 3 illustrates a schematic structural diagram of a liquid flow controller according to an embodiment of the present disclosure.

Now referring to FIG. 3, a schematic structural diagram of a liquid flow controller 200 according to some embodiments of the present disclosure is illustrated. As shown in FIG. 3, the liquid flow controller 200 may include a holder 210, an eccentric wheel 220, a micromotor 230, a second communication subassembly 240, and a second controller 250.

The holder 210 may have an open slot, wherein the first infusion tube 400 may be placed in the open slot. That is, a cross section of the holder 210 may be of U shape, and the first infusion tube 400 may be placed at the bottom of the U shape. The holder 210 can be made of any suitable rigid material (e.g., hard plastic, aluminum alloy, etc.) known to those skilled in the art.

The eccentric wheel 220 may be configured to turn off or on the first infusion tube 400, or regulate an infusion speed in the first infusion tube 400 by compressing or releasing the first infusion tube 400 by way of rotatably going into/out of the open slot. That is, the eccentric wheel 220 may be arranged at a suitable location on a side of the holder 210, such that when the eccentric wheel 220 is rotated about its center of rotation, its edge which is the furthest from the center of rotation can go into/out of the open slot, thereby enabling the first infusion tube 400 to be compressed and released, so as to turn on or off the first infusion tube 400 or regulate the infusion speed in the first infusion tube 400. The left view in FIG. 3 illustrates a case where the farthest edge of the eccentric wheel 220 goes out of the open slot, such that the first infusion tube 400 is released. The right view in FIG. 3 illustrates a case where the farthest edge of the eccentric wheel 220 goes into the open slot, such that the first infusion tube 400 is compressed. The eccentric wheel 220 and the holder 210 may be mounted together on a bracket (not shown). The eccentric wheel 220 may be made of any suitable rigid material (e.g., hard plastic, aluminum alloy, etc.) known to those skilled in the art.

The micromotor 230 may be configured to drive the eccentric wheel 220 to rotate under control of the second controller 250. The micromotor 230 may be any micromotor known to those skilled in the art. The micromotor 230 may be coupled to the eccentric wheel 220 in any way known to those skilled in the art (e.g., in coaxial or transmission way, etc.), such that the eccentric wheel 220 can be driven to rotate. The micromotor 230 may be in wired connection to the second controller 250 to receive a rotation control instruction from the second controller 250.

The second communication subassembly 240 may be communicatively coupled to the first communication subassembly 130 in the multi-port container assembly 100. The second communication subassembly 240 may be any wireless communication assembly known to those skilled in the art, such as a Bluetooth communication assembly or a WLAN communication assembly, etc., which may establish a wireless connection and intercommunicate with the first communication subassembly 130 in the multi-port container assembly 100. In some embodiments, the second communication subassembly 240 may also be a wired communication subassembly that establishes a wired connection and intercommunicates with the first communication subassembly 130 through a wired line.

The second controller 250 may be coupled to the micromotor 230 and the second communication subassembly 240, and may be configured to control the micromotor 230 to drive the eccentric wheel 220 to rotate to turn off or on the first infusion tube 400 in response to receiving the first signal from the first communication subassembly 130 via the second communication subassembly 240.

As described above, in some embodiments, the liquid flow controller 200 may include a plurality of the liquid flow controllers 200, and each of the liquid flow controllers 200 may be positioned on a first infusion tube 400 and may be configured to turn on or off the first infusion tube 400. In this case, the second communication subassembly 240 of each liquid flow controller 200 may be communicatively coupled to the first communication subassembly 130 in the multi-port container assembly 100. Thus, the second communication subassembly 240 in the liquid flow controller 200 on the first infusion tube 400 in current infusion may receive the first signal from the first communication subassembly 130, and in response, the second controller 250 in the liquid flow controller 200 may control the micromotor 230 to drive the eccentric wheel 220 to rotate to turn off the first infusion tube 400 in current infusion. Meanwhile, the second communication subassembly 240 in the liquid flow controller 200 for the next first infusion tube 400 also may receive the first signal from the first communication subassembly, and in response, the second controller 250 in the liquid flow controller 200 may control the micromotor 230 to drive the eccentric wheel 220 to rotate to turn on the next first infusion tube 400.

In some embodiments, the first controller 140 in the multi-port container assembly 100 may control the first communication subassembly 130 to send different control instructions to the second communication subassembly 240 in the liquid flow controller 200 for the first infusion tube 400 in current infusion and the second communication subassembly 240 in the liquid flow controller 200 for the next first infusion tube 400, to turn off the first infusion tube 400 in current infusion and turn on the next first infusion tube 400. In a further embodiment, infusion sequences for a plurality of first infusion tubes may be stored in the first controller 140 in the multi-port container assembly 100, and alternatively, the infusion sequences may be set by the user, for example, via a user interface coupled to the first controller 140.

The second controller 250 may be implemented by any processing unit having logic operation and processing functions. The processing unit typically has hardware processing circuits or chips, and software for programming the hardware circuits or chips to perform the respective functions. The software may be stored in a memory unit associated with the hardware processing circuits and loaded and executed by the hardware processing circuits, or may be solidified in the hardware processing circuits or chips. For example, the second controller 250 may be implemented by a microcontroller unit (MCU). The second controller 250 may be in wired connection to the micromotor 230, and may be positioned on a same printed circuit board as the second communication subassembly 240. In some embodiments, the liquid flow controller 200 may also include other subassemblies, such as a power supply subassembly (not shown) configured to supply power for the second controller 250, etc. The power supply subassembly may be positioned on the same printed circuit board as the second controller 250 and the second communication subassembly 240.

As further shown in FIG. 3, in some exemplary embodiments, each of the liquid flow controllers 200 further includes a timing component 260, configured to start timing under the control of the second controller 250 and notify the second controller 250 when a preset time value is reached. The second controller 250 is further configured to control the timing component 260 to start timing in response to receiving the first signal from the first communication subassembly 130, and control to turn on the first infusion tube in response to receiving a notification from the timing component 260 indicating that the timing reaches the preset time value. In these embodiments, when the liquid flow controller 200 receives the first signal from the first communication subassembly 130 of the multi-port container assembly 100, it may be determined that the liquid in the infusion container 500 currently connected with the multi-port container 110 is about to run out. At this moment, the liquid flow controller 200 does not immediately turn on the next infusion tube 400 under its control, but turns on the timing component 260 to start timing, and turns on the next infusion tube 400 under its control when the timing reaches the preset time value. Therefore, these embodiments are suitable for occasions where different pharmaceutical liquids are required for time-divisional infusion. Problem that different medicaments cannot be mixed for use or cannot be continuously infused can be solved, and thus intelligent infusion control solution of the present disclosure can be further improved.

The timing component 260 may be implemented by any clock circuit, chip, software, or any combination thereof, as is known in the art.

Referring back to FIG. 1, in some embodiments of the present disclosure, the infusion control device 10 may further include a wearable component 300. It is to be noted that in some other embodiments of the present disclosure, the infusion control device 10 may only include the multi-port container assembly 100 and the liquid flow controller 200, but does not include the wearable component 300.

In some embodiments, the wearable component 300 may be configured to detect a pulse of a person receiving infusion, and send a second signal to the liquid flow controller 200 in response to detecting an abnormal pulse of the person receiving infusion.

The liquid flow controller 200 may be further configured to reduce an infusion speed in the current first infusion tube 400 in response to receiving the second signal from the wearable component 300.

The wearable component 300 may be configured to cover a wrist of the person receiving infusion, such that the pulse of the person receiving infusion may be detected. In other embodiments, the wearable component 300 may also be configured to cover other body areas of the person receiving infusion that are adapted to detecting the pulse of the person receiving infusion. The second signal may be any electrical signal that has unique electrical characteristics and thus can be recognized.

The wearable component 300 may determine whether the pulse of the person receiving infusion is abnormal by determining whether the detected pulse of the person receiving infusion is changed significantly or by determining whether the detected pulse of the person receiving infusion is out of a normal range. For example, if the wearable component 300 detects that the pulse of the person receiving infusion is changed by above 10%, the pulse of the person receiving infusion can be determined as abnormal. Alternatively, if the pulse of the person receiving infusion is beyond the range of the normal human heart rate, the pulse of the person receiving infusion can also be determined as abnormal.

As mentioned previously, the second controller 250 in the liquid flow controller 200 for the first infusion tube 400 in current infusion may control, in response to the second signal, the micromotor 230 to drive the eccentric wheel 220 to rotate at a certain angle, to reduce the infusion speed in the first infusion tube 400.

In these embodiments of the present disclosure, the infusion speed can be reduced when the pulse of the person receiving infusion is detected to be abnormal, thereby further improving the safety of infusion.

Figure 4:
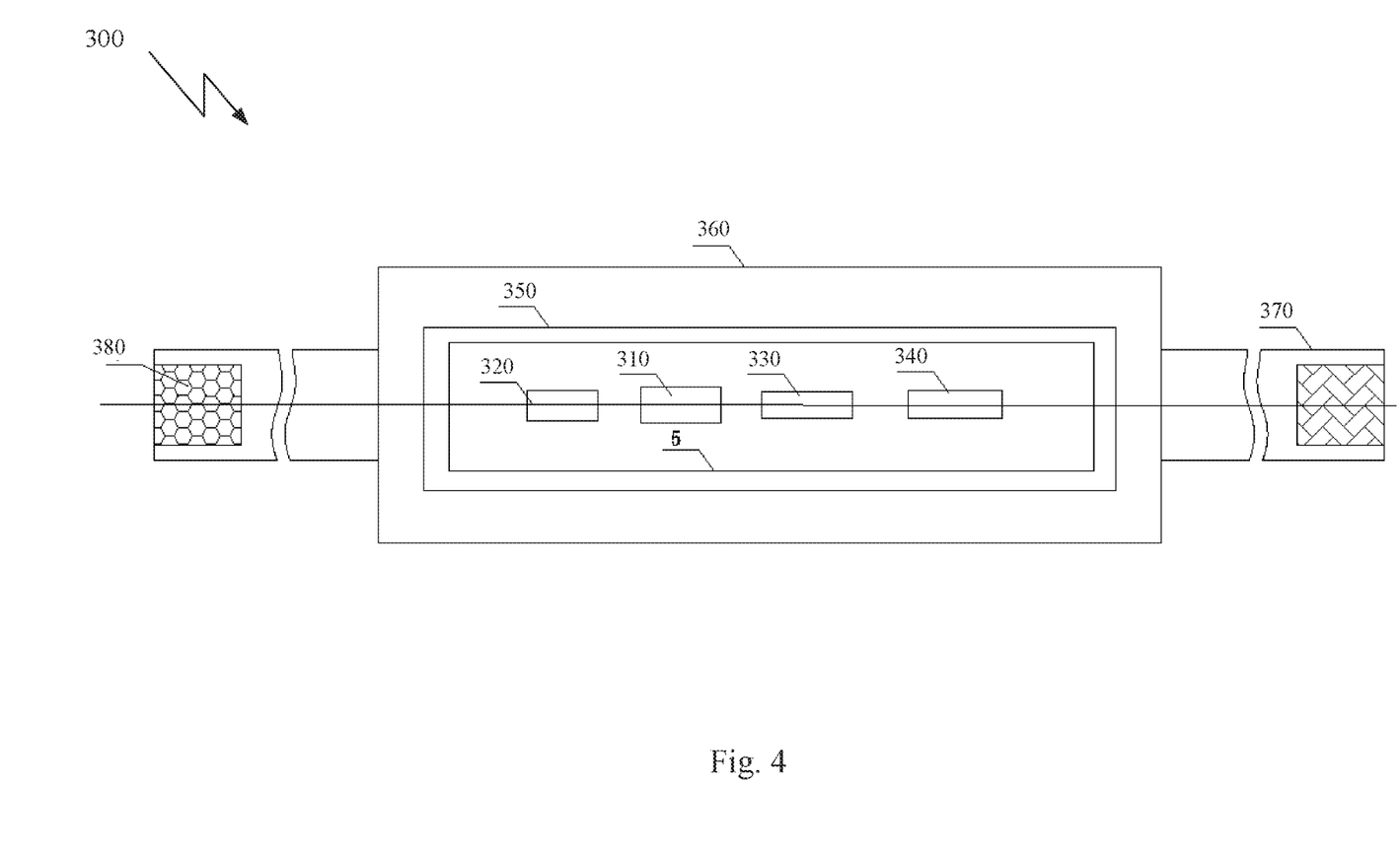
FIG. 4 illustrates a schematic structural diagram of a wearable component according to an embodiment of the present disclosure.

Now referring to FIG. 4, a schematic structural diagram of a wearable component 300 according to some embodiments of the present disclosure is illustrated. As shown in FIG. 4, the wearable component 300 includes a pulse sensor 310, a third communication subassembly 320, and a third controller 330.

The pulse sensor 310 may be configured to detect a pulse of a person receiving infusion. The pulse sensor 310 may be any pulse sensor known to those skilled in the art.

The third communication subassembly 320 may be communicatively coupled to the liquid flow controller 200. In some embodiments, the third communication subassembly 320 is communicatively coupled to the second communication subassembly 240 in the liquid flow controller 200. The third communication subassembly 320 may be any wireless communication assembly known to those skilled in the art, such as a Bluetooth communication assembly, a WLAN communication assembly, etc. The third communication subassembly 320 may establish a wireless connection with the second communication subassembly 240 in the liquid flow controller 200 and communicate with each other. In some embodiments, the third communication subassembly 320 may also be a wired communication subassembly that establishes a wired connection and intercommunicates with the second communication subassembly 240 through a wired line.

The third controller 330 may be coupled to the pulse sensor 310 and the third communication subassembly 320, and may be configured to send the second signal to the liquid flow controller 200 via the third communication subassembly 320 in response to detecting the abnormal pulse of the person receiving infusion by the pulse sensor 310, such that the liquid flow controller 200 reduces the infusion speed in the current first infusion tube 400.

In some other embodiments, the third communication subassembly 320 may also be communicatively coupled to the first communication subassembly 130 in the multi-port container assembly 100. The third controller 330 may be configured to send, in response to detecting the abnormal pulse of the person receiving infusion by the pulse sensor 310, the second signal to the first communication subassembly 130 in the multi-port container assembly 100 via the third communication subassembly 320. The first controller 140 in the multi-port container assembly 100 may forward the second signal to the liquid flow controller 200, such that the liquid flow controller 200 reduces the infusion speed in the current first infusion tube 400. Alternatively, the first controller 140 in the multi-port container assembly 100 may also process the second signal in other manner.

The third controller 330 may be implemented by any processing unit having logic operation and processing functions. The processing unit typically has hardware processing circuits or chips, and software for programming the hardware circuits or chips to perform the respective functions. The software may be stored in a memory unit associated with the hardware processing circuits and loaded and executed by the hardware processing circuits, or may be solidified in the hardware processing circuits or chips. For example, the third controller 330 may be implemented by a microcontroller unit (MCU). The third controller 330 may be in wired connection to the pulse sensor 310 and the third communication subassembly 320.

In some embodiments, the wearable component 300 may further include a second temperature sensor 340 and a second heating and thermal insulation layer 350.

The second temperature sensor 340 may be configured to detect temperature of the liquid for infusion near the infusion needle and transmit the detected temperature to the third controller 330.

The second temperature sensor 340 may be any temperature sensor known to those skilled in the art. For example, the second temperature sensor 340 may be arranged at a location of the wearable component 300, which is close to skin and the corresponds to the infusion needle of the second infusion tube 600, such that the temperature of the infusion liquid near the infusion needle may be detected.

The second heating and thermal insulation layer 350 may be configured to heat the infusion liquid near the infusion needle under control of the third controller 330.

The second heating and thermal insulation layer 350 may be arranged to cover, for example, the area of the second infusion tube 600 close to the infusion needle. The second heating and thermal insulation layer 350 may be composed of a layer of thermal insulation material and a heating device embedded into the thermal insulation material. The thermal insulation material may be any material having a thermal insulation function known to those skilled in the art, such as polyurethane, etc. The heating device may be any device having a heating function known to those skilled in the art, such as a resistive heater or a heating controller, etc.

The third controller 330 may be further coupled to the second temperature sensor 340 and the second heating and thermal insulation layer 350 by way of, for example, wired connection. The third controller 330 may be further configured to control the second heating and thermal insulation layer 350 to heat the infusion liquid near the infusion needle in response to the temperature detected by the second temperature sensor 340 being lower than a third predetermined threshold.

The third predetermined threshold may be set by a user in advance and stored in the third controller 330, or may be set by a manufacturer in advance and stored in the third controller 330. Specific value of the third predetermined threshold may be determined according to the temperature of the liquid as required during infusion. For example, the third predetermined threshold may be determined to be slightly higher than the normal body temperature of a human body or may be determined to be other temperatures which are most beneficial to human health. In some embodiments, the third predetermined threshold may be changed by the user according to actual needs during actual use of the device.

The infusion liquid near the infusion needle is heated by using the second temperature sensor 340 and the second heating and thermal insulation layer 350. In this way, it may effectively prevent reduction of the temperature of the infusion liquid in a transmitting process, ensuring the infusion liquid to be kept at temperature the most beneficial to human body health. Therefore, infusion safety can be further improved.

It is to be noted that the wearable component 300 may also include other subassemblies, such as a power supply subassembly (not shown) configured to supply power for the third controller 330, and the like.

In addition, as shown in FIG. 4, the wearable component 300 may be attached to, for example, a protective layer 360. A bandage 370 may be attached to two ends of the protective layer 360. An end of the bandage 370 may be provided with, for example, a magic tape 380, such that the bandage 370, the protective layer 360 and the wearable component 300 may be wrapped around a wrist of the person receiving infusion. The protective layer 360 may be made of any soft material (e.g., fabric, high molecular material) or the like, known to those skilled in the art. The bandage 370 may be made of any soft and elastic material (e.g., gauze, or the like.) known to those skilled in the art.

Referring back to FIG. 1, in some embodiments of the present disclosure, the infusion control device 10 may further include a setting component 700. It is to be noted that, in some other embodiments of the present disclosure, the infusion control device 10 may only include the multi-port container assembly 100 and the liquid flow controller 200, or may only include the multi-port container assembly 100, the liquid flow controller 200 and the wearable component 300, but does not include the setting component 700.

In some exemplary embodiments, the setting component 700 is configured to set at least one of a first predetermined threshold, an infusion sequence of the first infusion tube, a second predetermined threshold, a third predetermined threshold, and a preset time value. That is, the setting component 700 may be configured to set various parameters of the infusion control device 10 by a user (e.g., a medical professional or the like) to more effectively control the infusion process.

The number of the setting component 700 may be one or more. The setting component 700 may be communicatively coupled to the multi-port container assembly 100, the liquid flow controller 200, and the wearable component 300 in a wired or wireless manner.

In some exemplary embodiments, the setting component 700 may include a plurality of the setting components 700. The plurality of the setting components 700 are respectively arranged on the multi-port container assembly 100, the liquid flow controller 200 and the wearable component 300, and may be human-machine interaction interfaces electrically connected to the first controller 140, the second controller 250, and the third controller 330. The plurality of the setting components 700 respectively configured to provide current parameters (e.g., the first predetermined threshold, the second predetermined threshold, the third predetermined threshold, the infusion sequence, the preset time value, etc.) of the multi-port container assembly 100, the liquid flow controller 200, and the wearable component 300, and configured to set parameters of the multi-port container assembly 100, the liquid flow controller 200, and the wearable component 300. The setting component 700 may be implemented by any human-machine interaction interface known in the art. For example, the setting component 700 may include a display screen configured to display parameters, and a setting button configured to set the parameters.

In some other exemplary embodiments, the setting component 700 may include one setting component 700. The setting component 700 may be communicatively coupled to the multi-port container assembly 100, the liquid flow controller 200, and the wearable component 300 by way of wireless communication respectively. In these embodiments, the setting component 700 may be implemented by a computer, which may include a processor, a memory, an input/output device, and a communication device, and the like. Therefore, the current parameters of the multi-port container assembly 100, the liquid flow controller 200, and the wearable component 300 can be presented to the user. The parameters of the multi-port container assembly 100, the liquid flow controller 200, and the wearable component 300 can be set by the user. For example, the setting component 700 may be implemented by a monitoring device as described below or may be included in the monitoring device.

Figure 5:
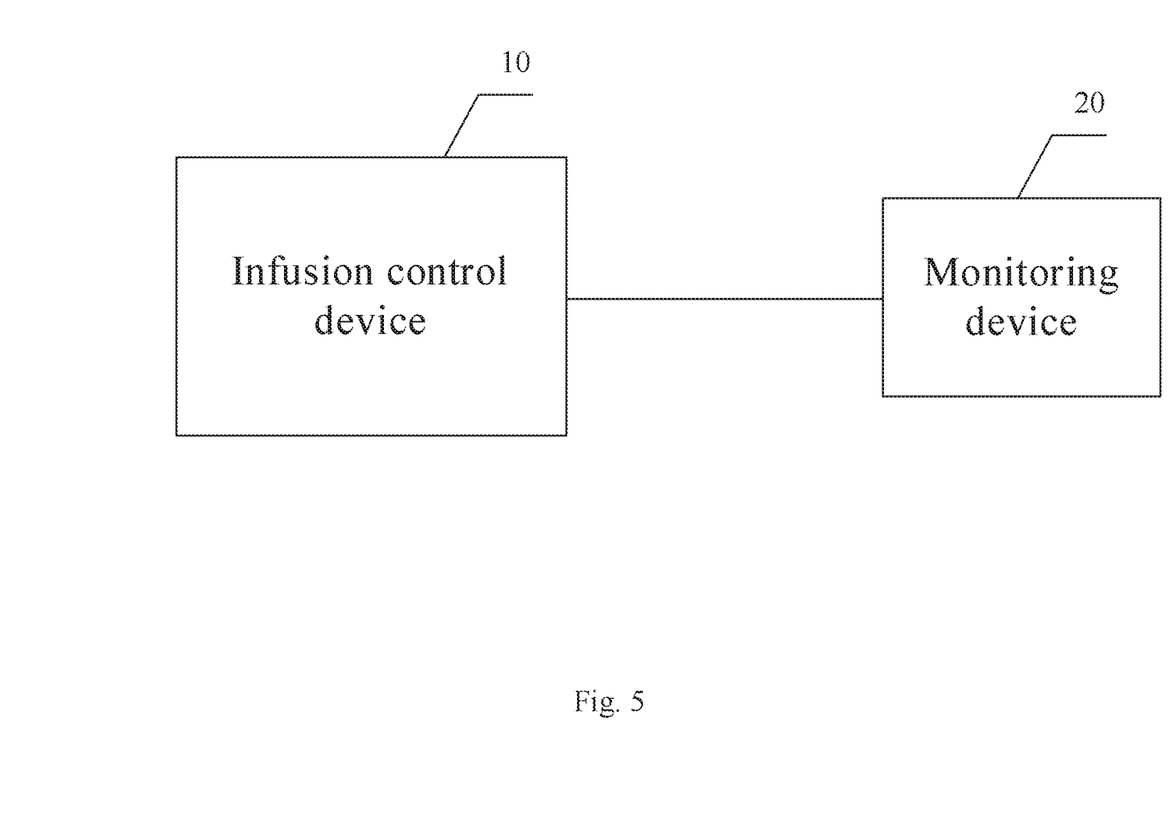
FIG. 5 illustrates a schematic block diagram of an infusion control apparatus according to an embodiment of the present disclosure.

Another aspect of the present disclosure further provides an infusion control apparatus. FIG. 5 illustrates a schematic block diagram of an infusion control apparatus according to an embodiment of the present disclosure. As shown in FIG. 5, the infusion control apparatus includes an infusion control device 10 according to any embodiment of the present disclosure, and a monitoring device 20. The monitoring device is configured to receive and present at least one of amount of liquid in the multi-port container 100 detected by the detector 120 from the multi-port container assembly 100 and temperature of the liquid in the multi-port container 100 detected by the first temperature sensor 150 of the multi-port container assembly 100, and/or is configured to receive and present at least one of a pulse of a person receiving infusion detected by the pulse sensor 310 of the wearable component 300 and temperature of the infusion liquid near the infusion needle detected by the second temperature sensor 340 of the wearable component 300.

In these embodiments of the present disclosure, the first controller 140 of the multi-port container 110 may also be configured to transmit, via the first communication subassembly 130, the amount of liquid in the multi-port container 100 detected by the detector 120 and/or the temperature of the liquid in the multi-port container 100 detected by the first temperature sensor 150 to the monitoring device 20.

Additionally, or alternatively, the third controller 330 in the wearable component 300 may also be configured to transmit, via the third communication subassembly 320, the pulse of the person receiving infusion detected by the pulse sensor 310 and/or the temperature of the infusion liquid near the infusion needle detected by the second temperature sensor 340 to the monitoring device 20.

By transmitting one or more of the detected the amount of liquid in the multi-port container 100, the temperature of the liquid in the multi-port container 100, the pulse of the person receiving infusion, and the temperature of the infusion liquid near the infusion needle to the monitoring device 20. In this way, the medical personnel can monitor the infusion process more conveniently via the monitoring device 20. Therefore, management of the infusion process can be further facilitated, and safety of infusion can be further improved.

In some exemplary embodiments, the monitoring device 20 is further configured to receive a first predetermined threshold set by a user, and send the first predetermined threshold to the multi-port container assembly 100, receive an infusion sequence of a first infusion tube 400 set by the user, and send the infusion sequence to a liquid flow controller 200, receive a second predetermined threshold set by the user, and send the second predetermined threshold to the multi-port container assembly 100, receive a third predetermined threshold set by the user, and send the third predetermined threshold to the wearable component 300, and receive a preset time value set by the user, and send the preset time value to the liquid flow controller.

That is, in these embodiments, the medical personnel may set parameters (for example, the first threshold, the second threshold, and the third threshold, or the like) of the infusion control device 10 via the monitoring device 20. Therefore, the medical personnel can manage the infusion process more conveniently and effectively to meet specific infusion requirements.

The monitoring device 20 may be implemented by, for example, a computer. The computer may include a processor and memory, an output device such as a display, an input device such as a mouse and keyboard, a wired or wireless communication device, and other computer components known to those skilled in the art. The memory may store a program causing the monitoring device 20 to perform its functions. The processor may perform the functions of the monitoring device 20 by loading and executing the program. For example, in a process of execution of the program, the processor may receive, via a wired or wireless communication device, data from the infusion control device 10, such as the amount of the liquid, the temperature of the liquid, and the pulse of the person receiving infusion, and display the received data (after being processed) on the display for the medical personnel to view. In addition, in the process of execution of the program, the display may display a graphical user interface under the control of the processor. The graphical user interface allows the user to set various parameters of the infusion control device 10. Then, may send the set parameters may be sent to the infusion control device 10 via a wired or wireless communication device.

The infusion control device 10 and the infusion control apparatus according to the embodiment of the present disclosure have been described above with reference to the accompanying drawings. It is to be noted that the above illustration and description is by way of example only and are not intended to be limiting of the present disclosure. In other embodiments of the present disclosure, the infusion control device 10 and the infusion control apparatus may have more, fewer, or different components. The relationship of location, connection, and functionality, or the like among the components may be different from what has been described and illustrated. For example, functionality performed by one component typically can also be accomplished by one or more different components. In addition, it can be noted that the names of the components in the present disclosure are merely for convenience of description, and are not intended to limit the present disclosure.

By reading the above description, those skilled in the art may know that still another aspect of the present disclosure also provides an infusion control method. The infusion control method may be performed by the infusion control device 10 or the infusion control apparatus according to the above embodiments of the present disclosure. Therefore, each step of the infusion control method corresponds to an operation of each component of the infusion control device 10 or the infusion control apparatus. Alternatively, the infusion control method may also be performed by other devices. For the sake of brevity, some details repeated with the above descriptions are omitted in the following descriptions. Therefore, more details of the method for controlling infusion may be obtained with reference to the above descriptions.

Figure 6:
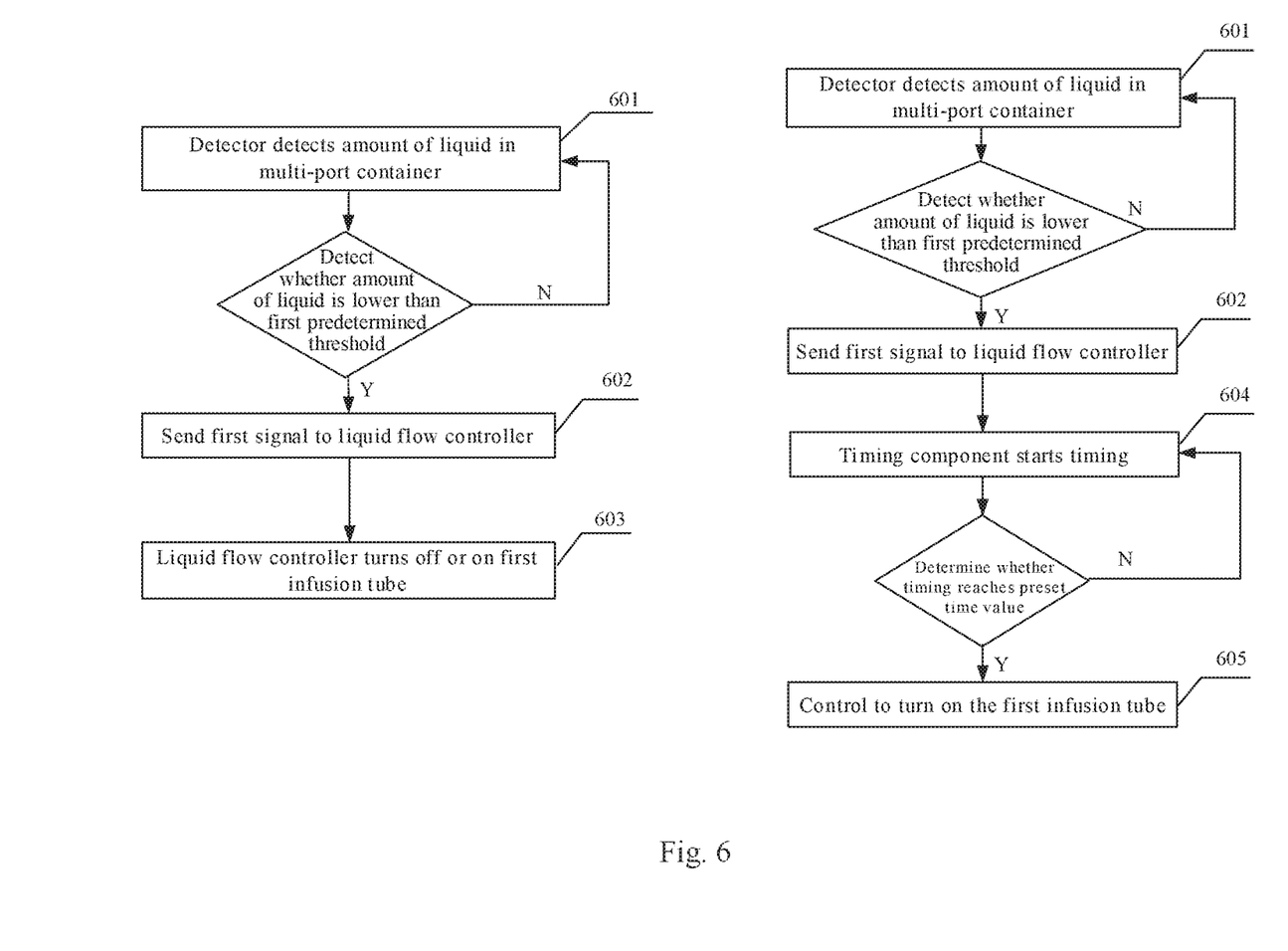
FIG. 6-FIG. 9 schematically illustrate aspects of an infusion control method according to an embodiment of the present disclosure respectively.

Now referring to FIG. 6-FIG. 9, a plurality of aspects of an infusion control method according to an embodiment of the present disclosure are schematically illustrated, respectively. As shown in FIG. 6, the infusion control method includes following steps.

In Step 601, a detector detects amount of liquid in a multi-port container. The multi-port container has a plurality of inlets and an outlet. Each of the inlets is connected with an infusion container via a first infusion tube, and the outlet is connected with an infusion needle via a second infusion tube.

In Step 602, a first signal is sent to a liquid flow controller in response to the detector detecting that the amount of liquid is lower than a first predetermined threshold.

In Step 603, the liquid flow controller turns off or on the first infusion tube in response to receiving the first signal.

In some exemplary embodiments, the Step 603 of turning off or on the first infusion tube by the liquid flow controller in response to receiving the first signal includes turning off a current first infusion tube and turning on a next first infusion tube by the liquid flow controller in response to receiving the first signal.

In some exemplary embodiments, the liquid flow controller includes a plurality of the liquid flow controllers, and each of the liquid flow controllers is configured to control the first infusion tube to be turned on or off.

In some exemplary embodiments, the Step 603 of turning off or on the first infusion tube by the liquid flow controller in response to receiving the first signal includes following steps. That is, the Step 603 can be substituted by following steps.

In Step 604, a timing component starts timing in response to receiving the first signal.

In Step 605, the first infusion tube is turned on in response to the timing component indicating that the timing reaches a preset time value.

Figure 7:
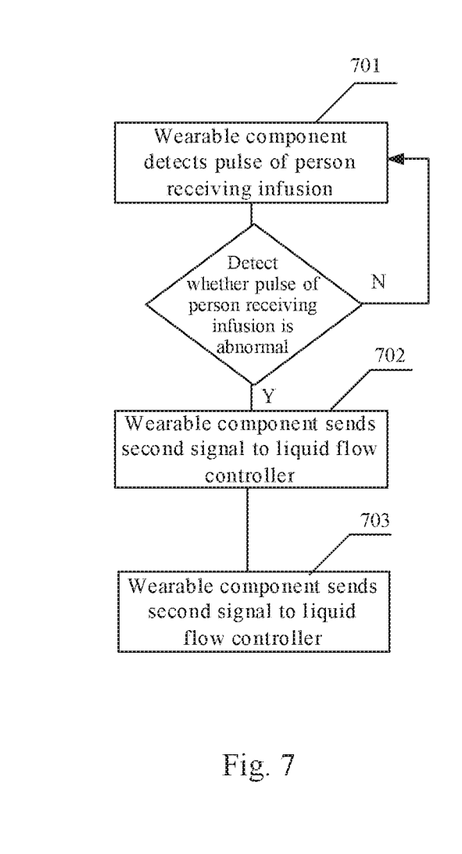

As shown in FIG. 7, in some exemplary embodiments, the infusion control method includes following steps.

In Step 701, a wearable component detects a pulse of a person receiving infusion.

In Step 702, the wearable component sends a second signal to the liquid flow controller in response to detecting an abnormal pulse of the person receiving infusion.

In Step 703, the liquid flow controller reduces infusion speed in the current first infusion tube in response to receiving the second signal from the wearable component.

Figure 8:
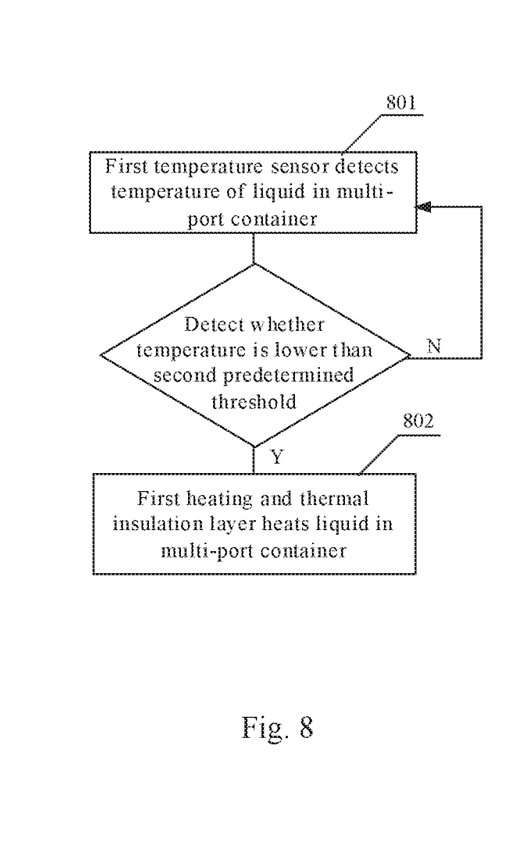

As shown in FIG. 8, in some exemplary embodiments, the infusion control method includes following steps.

In Step 801, a first temperature sensor detects temperature of liquid in the multi-port container.

In Step 802, a first heating and thermal insulation layer heats the liquid in the multi-port container in response to the temperature of the liquid in the multi-port container detected by the first temperature sensor being lower than a second predetermined threshold.

Figure 9:
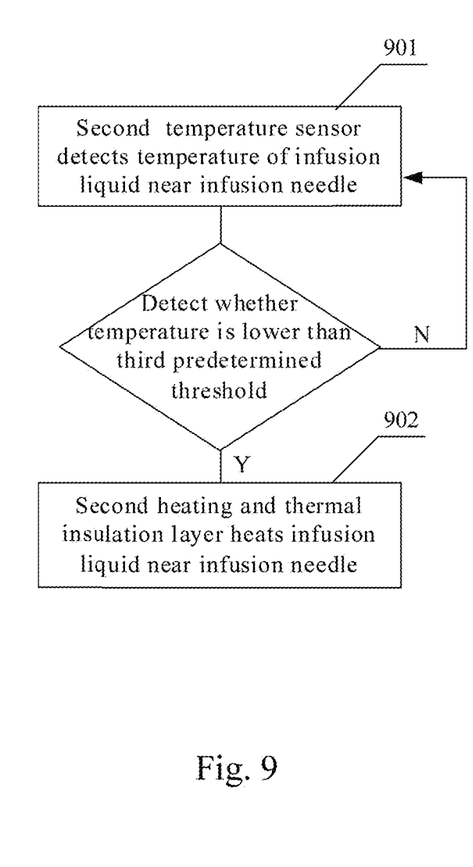

As shown in FIG. 9, in some exemplary embodiments, the infusion control method includes following steps.

In Step 901, a second temperature sensor detects temperature of the infusion liquid near the infusion needle.

In Step 902, a second heating and thermal insulation layer heats the infusion liquid near the infusion needle in response to the temperature detected by the second temperature sensor being lower than a third predetermined threshold.

In some exemplary embodiments, the infusion control method further includes at least one of following steps: presenting amount of liquid in a multi-port container detected by the detector, presenting temperature of the liquid in the multi-port container detected by the first temperature sensor, presenting a pulse of a person receiving infusion detected by the pulse sensor, and presenting temperature of the infusion liquid near the infusion needle detected by the second temperature sensor.

It is to be noted that, in the above infusion control method according to the embodiments of the present disclosure, a group of Steps 601, 602, and 603, a group of Steps 601, 602, 604, and 605, a group of Steps 701 and 702, a group of Steps 801 and 802, and a group of Steps 901 and 902 actually represent a plurality of mutually independent aspects of the infusion control method. Therefore, the infusion control method may include any one or more of these groups of steps, and an execution sequence between a plurality of groups of steps may be arbitrary.

It is to be understood that some assemblies or subassemblies in the embodiments of the present disclosure may be implemented as a combination of a processor and a memory. The processor executes a program stored in the memory to implement functions of the corresponding assemblies or subassemblies. The assemblies or subassemblies described herein may also be implemented in entirely hardware embodiments, including an application-specific integrated circuit (ASIC) or a field programmable gate array (FPGA), etc.

It can also be noted that although the infusion control method according to the embodiments of the present disclosure has been described above with reference to the accompanying drawings, the above illustration and description is by way of example only and is not intended to be limiting of the present disclosure. In other embodiments of the present disclosure, the infusion control method may have more, fewer, or different steps, and the relationship of sequences, inclusion, and functionality etc. among the parts may be different from what has been described and illustrated. For example, generally one step may be divided into a plurality of smaller steps, and a plurality of steps may be combined into one larger step.

The foregoing description of the embodiments of the present disclosure has been provided for the purpose of illustration and description. Numerous specific details are set forth such as examples of specific components and devices, to provide a thorough understanding of embodiments of the present disclosure. It is not intended to be exhaustive or to limit the present disclosure. Various components or features of specific embodiments generally are not limited to specific embodiments. However, these components and features are interchangeable and may be used in other embodiments without specific illustration or description, where appropriate. Such variations are not to be regarded as a departure from the present disclosure, and all such modifications are intended to be included within the scope of the present disclosure. In some exemplary embodiments, well-known components, well-known structures, and well-known technologies are not described in detail.

The terminology used herein is for the purpose of describing particular exemplary embodiments only and is not intended to be restrictive. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The steps, processes, and operations described herein are not to be construed as necessarily requiring their performance in the particular order discussed or illustrated, unless specifically identified as an order of performance.

When an element or layer is referred to as being "on", "engaged to", "connected to" or "coupled to" another element or layer, it may be directly on, engaged, connected or coupled to the other element or layer, or intervening elements or layers may be present. Other words used to describe the relationship between elements should be interpreted in a like fashion (e.g., "between" versus "directly between," "adjacent" versus "directly adjacent," etc.). As used herein, it is to be noted that unless explicitly specified or limited otherwise, "connecting", "coupling" or similar terms may refer to one or more of a mechanical connection, an electrical connection and a communication connection. In addition, as used herein, the term "and/or" includes any and all combinations of one or more of the associated listed items.

Although the terms first, second, third, etc. may be used herein to describe various elements, components, layers, and/or sections, these elements, components, layers, and/or sections should not be limited by these terms. These terms are only used to distinguish one element, component, layer, or section from another element, component, layer, or section. Terms such as "first," "second," and other numerical terms when used herein do not imply a sequence or order unless clearly indicated by the context. Thus, a first element, component, layer or section in the present disclosure may be termed a second element, component, layer, or section without departing from the teachings of the exemplary embodiments.

Spatially relative terms, such as "inner," "outer," "beneath", "below", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" may encompass both an orientation of above and below. The device may be otherwise oriented (rotated 90 degrees or at other orientations) and the spatially relative descriptors used herein should be interpreted accordingly.

It is to be understood that the foregoing embodiments of the present disclosure are merely exemplary embodiments employed to describe the principles of the present disclosure. However, the present disclosure is not limited thereto. For those of ordinary skill in the art, various modifications and improvements may be made without departing from the spirit and essence of the present disclosure, and these modifications and improvements are also deemed to be within the scope of protection of the present disclosure. The scope of protection of the present disclosure is limited only by the meaning of the language expression of the appended claims and their equivalents.

What is claimed is:

1. A device for controlling infusion, comprising a multi-port container assembly and a liquid flow controller,
wherein the multi-port container assembly comprises:
a multi-port container having a plurality of inlets and an outlet, each of the plurality of inlets connected with an infusion container via a corresponding first infusion tube, the outlet connected with an infusion needle via a second infusion tube;

a detector, configured to detect an amount of liquid in the multi-port container;

a first communication subassembly, communicatively coupled to the liquid flow controller; and a first controller, coupled to the detector and the first communication subassembly, and configured to send a first signal to the liquid flow controller via the first communication subassembly in response to the detector detecting that the amount of liquid is lower than a first predetermined threshold; and wherein the liquid flow controller is configured to turn on or off each respective corresponding first infusion tube in response to receiving the first signal from the first communication subassembly;

wherein the device further comprises a wearable component, which comprises:

a third communication subassembly, communicatively coupled to the liquid flow controller;

a third controller, coupled to the third communication subassembly;

a second temperature sensor, configured to detect a temperature of infusion liquid near the infusion needle and to transmit the detected temperature to the third controller;

a second heating and thermal insulation layer, configured to heat the infusion liquid near the infusion needle under control of the third controller; and a pulse sensor, configured to detect a pulse of a person receiving infusion;

wherein the third controller is coupled to the second temperature sensor and the second heating and thermal insulation layer, and is configured to control the second heating and thermal insulation layer to heat the infusion liquid near the infusion needle in response to the temperature detected by the second temperature sensor being lower than a third predetermined threshold;

wherein the third controller is further coupled to the pulse sensor, and further configured to send a second signal to the liquid flow controller via the third communication subassembly in response to detecting an abnormal pulse of the person receiving infusion; and wherein the liquid flow controller is further configured to reduce an infusion speed in a respective one of the corresponding first infusion tubes currently turned on in response to receiving the second signal from the wearable component.

2. The device according to claim 1, wherein the liquid flow controller is further configured to turn off a respective one of the corresponding first infusion tubes currently turned on and to turn on another one of the corresponding first infusion tubes currently turned off in response to receiving the first signal from the first communication subassembly.

3. The device according to claim 1, wherein the liquid flow controller comprises a plurality of the liquid flow controllers, and each of the plurality of the liquid flow controllers is configured to turn on or off a respective one of the corresponding first infusion tubes.

4. The device according to claim 3, wherein each of the liquid flow controllers comprises:

a holder having an open slot, wherein the respective one of the corresponding first infusion tubes is placed in the open slot;

an eccentric wheel, configured to turn on or off the respective one of the corresponding first infusion tubes, or to regulate an infusion speed in the respective one of the corresponding first infusion tubes by compressing or releasing the respective one of the corresponding first infusion tubes by way of rotatably going into or out of the open slot;

a micromotor, configured to drive the eccentric wheel to rotate under control of a second controller;

a second communication subassembly, communicatively coupled to the first communication subassembly; and the second controller, coupled to the micromotor and the second communication subassembly, and configured to control the micromotor to drive the eccentric wheel to rotate to turn on or off the respective one of the corresponding first infusion tubes in response to receiving the first signal from the first communication subassembly via the second communication subassembly.

5. The device according to claim 4, wherein each of the liquid flow controllers further comprises:

a timing component, configured to start timing under the control of the second controller and to notify the second controller when a preset time value is reached;

wherein the second controller is further configured to control the timing component to start timing in response to receiving the first signal from the first communication subassembly, and to turn on the respective one of the corresponding first infusion tubes in response to receiving a notification from the timing component indicating that the timing has reached the preset time value.

6. The device according to claim 1, wherein the multi-port container assembly further comprises:

a first temperature sensor, coupled to the first controller and configured to detect a temperature of the liquid in the multi-port container and to transmit the detected temperature from the first temperature sensor to the first controller; and a first heating and thermal insulation layer, coupled to the first controller and configured to heat the liquid in the multi-port container under control of the first controller;

wherein the first controller is further configured to control the first heating and thermal insulation layer to heat the liquid in the multi-port container in response to the temperature of the liquid in the multi-port container detected by the first temperature sensor being lower than a second predetermined threshold.

7. The device according to claim 1, wherein the detector comprises a pressure sensor, and wherein the amount of liquid is represented by a liquid pressure of the multi-port container detected by the pressure sensor.

8. An apparatus for controlling infusion comprising:

a device for controlling infusion according to claim 1; and a monitoring device, configured to at least one of i) receive and present at least one of the amount of liquid in the multi-port container detected by the detector from the multi-port container assembly and a temperature of the liquid in the multi-port container detected by a first temperature sensor of the multi-port container assembly, and ii) receive and present at least one of the pulse of the person receiving infusion detected by the pulse sensor of the wearable component and the temperature of the infusion liquid near the infusion needle detected by the second temperature sensor of the wearable component.

9. The apparatus according to claim 8, wherein the monitoring device is further configured to:

receive the first predetermined threshold preset by a user, and to send the first predetermined threshold to the multi-port container assembly;

receive an infusion sequence of one of the corresponding first infusion tubes, and to send the infusion sequence to the liquid flow controller;

receive a second predetermined threshold, and to send the second predetermined threshold to the multi-port container assembly;

receive the third predetermined threshold, and to send the third predetermined threshold to the wearable component; and receive a preset time value and to send the preset time value to the liquid flow controller.

10. The apparatus according to claim 8, wherein a liquid flow controller of the device for controlling infusion is further configured to turn off the respective one of the corresponding first infusion tubes currently turned on and to turn on a next respective one of the corresponding first infusion tubes in response to receiving the first signal from the first communication subassembly.

11. A method for controlling infusion comprising:
de­tecting, by a detector, an amount of liquid in a multi-port container, wherein the multi-port container has a plurality of inlets and an outlet, each of the plurality of inlets is connected with an infusion container via a corresponding first infusion tube, and the outlet is connected with an infusion needle via a second infusion tube;

sending a first signal to a liquid flow controller in response to the detector detecting that the amount of liquid is lower than a first predetermined threshold; and turning on or off a respective one of the corresponding first infusion tubes by the liquid flow controller in response to receiving the first signal;

detecting, by a second temperature sensor, temperature of infusion liquid near the infusion needle; and heating, by a second heating and thermal insulation layer, the infusion liquid near the infusion needle in response to the temperature detected by the second temperature sensor being lower than a third predetermined threshold.

12. The method according to claim 11, wherein the turning on or off the respective one of the corresponding first infusion tubes by the liquid flow controller in response to receiving the first signal comprises:
turning off a respective one of the corresponding first infusion tubes currently turned on and turning on a next respective one of the corresponding first infusion tubes currently turned off by the liquid flow controller in response to receiving the first signal.

13. The method according to claim 11, wherein the liquid flow controller comprises a plurality of liquid flow controllers, wherein each of the plurality of liquid flow controllers is configured to turn on or off the respective one of the corresponding first infusion tubes, and wherein the turning on or off the respective one of the corresponding first infusion tubes by each of the plurality of liquid flow controllers in response to receiving the first signal comprises:
starting timing by a timing component in response to receiving the first signal; and turning on the respective one of the corresponding first infusion tubes in response to the timing component indicating that the timing has reached a preset time value.

14. The method according to claim 11, further comprising:
detecting, by a wearable component, a pulse of a person receiving infusion, and sending, by the wearable component, a second signal to the liquid flow controller in response to detecting an abnormal pulse of the person receiving infusion; and reducing, by the liquid flow controller, an infusion speed in a respective one of the corresponding first infusion tubes currently turned on in response to receiving the second signal from the wearable component.

15. The method according to claim 11, further comprising:
detecting, by a first temperature sensor, temperature of the liquid in the multi-port container; and heating, by a first heating and thermal insulation layer, the liquid in the multi-port container in response to the temperature of the liquid in the multi-port container detected by the first temperature sensor being lower than a second predetermined threshold.

16. The method according to claim 11, further comprising at least one of:
presenting the amount of the liquid in the multi-port container detected by the detector;

presenting a temperature of the liquid in the multi-port container detected by a first temperature sensor;

presenting a pulse of a person receiving infusion detected by a pulse sensor; and presenting temperature of the infusion liquid near the infusion needle detected by the second temperature sensor.

* * * * *